(12) United States Patent
Johansson

(10) Patent No.: US 10,610,698 B2
(45) Date of Patent: Apr. 7, 2020

(54) METHOD AND APPARATUS FOR CONTROLLING A LASER PROBE

(71) Applicant: Susanne Johansson, Stockholm (SE)

(72) Inventor: Susanne Johansson, Stockholm (SE)

(*) Notice: Subject to any disclaimer, the term of this patent is extended or adjusted under 35 U.S.C. 154(b) by 162 days.

(21) Appl. No.: 15/027,795

(22) PCT Filed: Oct. 7, 2014

(86) PCT No.: PCT/SE2014/051162
§ 371 (c)(1),
(2) Date: Apr. 7, 2016

(87) PCT Pub. No.: WO2015/053694
PCT Pub. Date: Apr. 16, 2015

(65) Prior Publication Data
US 2016/0228724 A1 Aug. 11, 2016

(30) Foreign Application Priority Data
Oct. 7, 2013 (SE) ...................................... 1351180

(51) Int. Cl.
*A61N 5/06* (2006.01)
*A61N 5/067* (2006.01)

(52) U.S. Cl.
CPC ...... *A61N 5/0613* (2013.01); *A61N 2005/067* (2013.01); *A61N 2005/0626* (2013.01);
(Continued)

(58) Field of Classification Search
CPC .......... A61N 5/0613; A61N 2005/0626; A61N 2005/0643; A61N 2005/0659; A61N 2005/0662; A61N 2005/067; A61N 5/0616
(Continued)

(56) References Cited

U.S. PATENT DOCUMENTS 6,755,820 B1* 6/2004 Johansson ............ A61N 5/0616
606/13
2001/0041884 A1* 11/2001 Frey .................... A61F 9/00806
606/5
(Continued)

FOREIGN PATENT DOCUMENTS

CN 101267845 A 9/2008
CN 102811768 A 12/2012
(Continued)

OTHER PUBLICATIONS

International Search Report for corresponding Swedish Patent Application No. PCT/SE2014/051162 dated Apr. 1, 2015.
(Continued)

*Primary Examiner* — Michael W Kahelin
*Assistant Examiner* — Vynn V Huh
(74) *Attorney, Agent, or Firm* — Renner, Otto, Boisselle & Sklar, LLP

(57) ABSTRACT

A device for controlling a low level laser probe (20a) suitable for treating adult stem cells of a subject, said probe (20) having a plurality of light sources ($24_a \ldots 24_n$) provided in a doming treatment surface (25). The device receives, stores and provides (11a, 11) status information from a subject and in accordance with the status information provided controls (12) the laser probe (20a) to transmit visible light ($\lambda$) having at least two various wavelengths ($\lambda_1 \ldots \lambda_n$) for stimulating adult stem cells of the subject, wherein at least one first light source (24a) being centrally positioned in the doming treatment surface (25) of the probe (20a) is adapted to transmit light of a first wavelength ($\lambda_1$) of a first particular intensity ($I_1$) and the other light sources ($24_n$) positioned around the first light source (24a) are adapted to transmit light of another higher wavelength ($\lambda_n$) and at least a second higher intensity ($I_2$).

5 Claims, 2 Drawing Sheets

Figure 1:
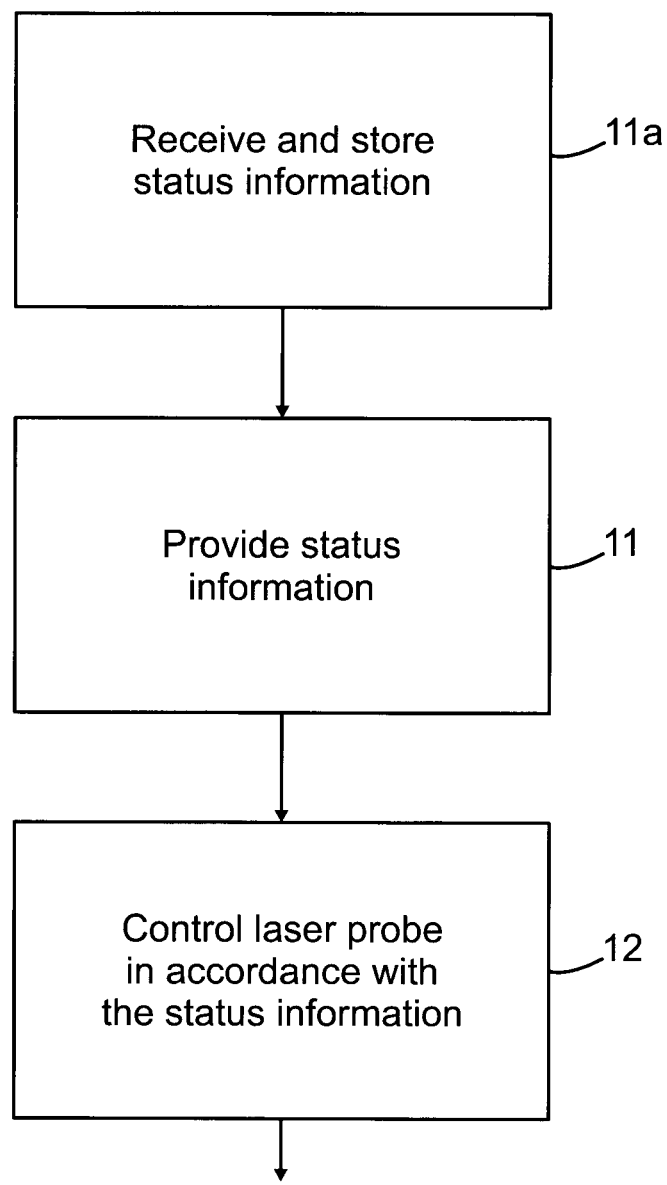

(52) U.S. Cl.
CPC ............... *A61N 2005/0643* (2013.01); *A61N 2005/0659* (2013.01); *A61N 2005/0662* (2013.01)

(58) Field of Classification Search
USPC ...................................................... 607/88–94
See application file for complete search history.

(56) References Cited

U.S. PATENT DOCUMENTS

| | | | |
|---|---|---|---|
| 2002/0002391 A1 | 1/2002 | Gerdes | |
| 2004/0030370 A1 | 2/2004 | Lytle | |
| 2006/0184214 A1 | 8/2006 | McDaniel | |
| 2007/0208395 A1* | 9/2007 | Leclerc | A61N 5/0616 607/86 |
| 2007/0213792 A1* | 9/2007 | Yaroslavsky | A61N 5/0613 607/100 |
| 2009/0299441 A1 | 12/2009 | Bornstein | |
| 2011/0060266 A1 | 3/2011 | Streeter et al. | |
| 2011/0144725 A1 | 6/2011 | Pryor et al. | |
| 2011/0178583 A1 | 7/2011 | Gerlitz et al. | |
| 2013/0344560 A1 | 12/2013 | Weston et al. | |

FOREIGN PATENT DOCUMENTS

| | | |
|---|---|---|
| CN | 102844075 A | 12/2012 |
| CN | 102905750 A | 1/2013 |
| EP | 0 320 080 A1 | 6/1989 |
| EP | 0320080 A1 | 6/1989 |
| WO | 01/21256 A1 | 3/2001 |
| WO | 2013/120095 A1 | 8/2013 |

OTHER PUBLICATIONS

Office Action for corresponding Chinese Patent Application No. 201480058952.7 dated Jun. 2, 2017.
Extended European Search Report for corresponding Patent Application No. 14852679.1 dated Apr. 13, 2017.
Office Action for corresponding Chinese Patent Application No. 201480058952.7 dated Feb. 5, 2018.

* cited by examiner

METHOD AND APPARATUS FOR CONTROLLING A LASER PROBE

FIELD OF THE INVENTION

The present invention relates to a method and apparatus according to the preamble of the independent claims.

BACKGROUND OF THE INVENTION

Stem cells are defined by the ability to continuously self-renew and produce the differentiated progeny of the tissue of their location (Morrison et al., 1997). Adult stem cells are undifferentiated cells that reside in differentiated tissues, and have the properties of self-renewal and generation of differentiated cell types. The differentiated cell types may include all or some of the specialized cells in the tissue. Sources of stem cells include bone marrow, blood, the cornea and the retina of the eye, brain, skeletal muscle, dental pulp, liver, skin, the lining of the gastrointestinal tract, and pancreas. Adult stem cells make up a small percentage of the total cells. For instance, in the small intestine there are perhaps up to 10 stem cells at the bottom of the crypt out of a total crypt population of <300 cells. In skeletal muscle, satellite (stem) cells comprise about 5% of all nuclei, but in the bone marrow the multi-potential hematopoietic stem cell is much rarer, with a frequency of perhaps 1 in 10000 amongst all bone marrow cells. Considerable overlap exists between different putative organ specific stem cells in their repertoire of gene expression, often related to self-renewal, cell survival, and cell adhesion. However, the conditions to grow or simply 'select' stem cells in vitro do not exist for many tissues where it is accepted that the stem cells simply fail to grow due to lack of required growth factors or substrates. In many tissues, the stem cells have simply not been identified.

Nevertheless stem cells have been used routinely for more than three decades to repair tissues and organs damaged by injury or disease. While early, embryonic stem cells have generated considerable interest, adult stem cells are critical for tissue homeostasis and wound repair and reside within specific niches that preserve proliferative and regenerative potential (Blanpain and Fuchs, 2006; Moore and Lemischka, 2006).

Thus, understanding how stem cells are maintained, stimulated and participate in regeneration is important to combat a wide variety of diseases.

Stem cell therapy is a type of intervention strategy that introduces new adult stem cells into damaged tissue in order to treat a disease or an injury. Many medical researchers believe that stem cell treatments have the potential to change the face of human disease and alleviate suffering. The ability of stem cells stem to self-renew and give rise to subsequent generations with variable degrees of differentiation capacities offers significant potential for generation of tissues that can potentially replace diseased and damaged areas in the body, with minimal risk of rejection and side effects.

Today, a number of stem cell therapies exist, but most are only at experimental stages or is costly. But, medical researchers anticipate that stem cell therapy will probably be able to treat cancer, type 1 diabetes, Parkinson's disease, Huntington's disease, Celiac Disease, cardiac failure, muscle damage and neurological disorders, and many others. Nevertheless, before stem cell therapeutics can be applied in the clinical setting, more research is necessary to understand stem cell behavior upon transplantation as well as the mechanisms of stem cell interaction with the diseased/injured microenvironment.

For over 30 years, bone marrow, and more recently, umbilical cord blood stem cells, has been used to treat cancer patients with conditions such as leukemia and lymphoma. During chemotherapy, most growing cells are killed by the cytotoxic agents. These agents, however, cannot discriminate between the leukemia or neoplastic cells, and the hematopoietic cells within the bone marrow. It is this side effect of conventional chemotherapy strategies that the stem cell transplant attempts to reverse in that a donor's healthy bone marrow reintroduces functional stem cells to replace the cells lost in the host's body during treatment.

In the following, a number of known treatments are discussed.

Stroke and traumatic brain injury lead to cell death, characterized by a loss of neurons and oligodendrocytes within the brain. Healthy adult brains contain neural stem cells which divide to maintain general stem cell numbers, or become progenitor cells. In healthy adult animals, progenitor cells migrate within the brain and function primarily to maintain neuron populations for olfaction (the sense of smell). In pregnancy and after injury, this system appears to be regulated by growth factors and can increase the rate at which new brain matter is formed. Although the reparative process appears to initiate following trauma to the brain, substantial recovery is rarely observed in adults, suggesting a lack of robustness.

Stem cells may also be used to treat brain degeneration, such as in Parkinson's and Alzheimer's disease.

The development of gene therapy strategy for treatment of intra-cranial tumors offers much promise, and has shown to be successful. Using conventional techniques, brain cancer is difficult to treat because it spreads so rapidly. Researchers at the Harvard Medical School transplanted human neural stem cells into the brain of rodents that received intracranial tumors. Within days, the cells migrated into the cancerous area and produced cytosine deaminase, an enzyme that converts a non-toxic pro-drug into a chemotherapeutic agent. As a result, the injected substance was able to reduce the tumor mass by 81 percent. The stem cells neither differentiated nor turned tumorigenic—Some researchers believe that the key to finding a cure for cancer is to inhibit proliferation of cancer stem cells. Accordingly, current cancer treatments are designed to kill cancer cells. However, conventional chemotherapy treatments cannot discriminate between cancerous cells and others. Stem cell therapies may serve as potential treatments for cancer. Research on treating Lymphoma using adult stem cells is underway and has had human trials. Essentially, chemotherapy is used to completely destroy the patient's own lymphocytes, and stem cells injected, eventually replacing the immune system of the patient with that of the healthy donor.

Successful immune modulation by cord blood stem cells and the resulting clinical improvement in patient status may have important implications for other autoimmune and inflammation-related diseases.

However, there is still a need to better use stem cell therapy for curing diseases and other disorders. For this purpose, apparatus such as lasers have been used.

The use of lasers within science and medicine for the treatment of diseases, in particular the above mentioned diseases, and in therapy is currently widespread. Many researchers and research groups are performing experiments concerning tissue reactions in vitro in order to survey, predict and explain the effects of laser irradiation. Other researchers carry out tests in vivo on animals. Clinical research and clinical treatment have also been documented.

Therapeutic lasers used in medicine, for instance for stem cell therapy, generally fall into two categories: non-destructive, low-energy lasers, also referred to as "cold lasers" designed to generate largely thermal biological effects in tissue, and destructive lasers designed to selectively damage or destroy tissue.

The first category of laser, referred to as cold laser or low-level laser, typically use very low power density or irradiation. These low level lasers are used, for example, in laser therapy for stimulating cellular processes that are important in cellular regeneration and repair. Typically, a low level laser is designed to work through photochemical mechanisms and cause almost imperceptible changes in the temperature of the cells subject to such lasers. In essence, until now, low level lasers have only been used for thermal medical treatment. Typical maximum effective irradiances are within the range of about 1-45 mW/cm$^2$. Above this range a biological effect dose-response is often reported to be negative.

The second type of laser, the destructive so-called "high-level laser" will not be described in more detail herein this disclosure.

Treatment with low level lasers will not be discussed in more detail here, and the reader is referred to scientific studies and similar, such as "Isolated Neuron Response to Blue Laser Micro irradiation: Phenomenology and Possible Mechanism", A. B. Uzdensky, Department of Biophysics and Bio cybernetics, Physical Faculty, Rostov State University, Stachky av., 194/1, Rostov-on-Don. 344090, Russia and Rochkind S. (1992) "Spinal Cord and Brain transplantation benefited by low-power laser irradiation". Lasers in Medical Science 7: 143-115.

Typically, a therapist who performs a low level laser treatment has many years of experience and must know where to apply radiation to tissue and how much to apply, for example, with respect to the power of the laser measured in milliwatts (mW), and which wavelength of light is most suitable for different types of treatment. This may be troublesome since there is often a need for sufficiently trained and experienced therapists. Even a very experienced therapist may suffer from sufficient training and experience to be able to control the laser probe properly.

SUMMARY OF THE INVENTION

An object of the present invention is to provide an improved method for controlling a low level laser probe adapted for stimulating stem cells of a subject and a control apparatus configured to control the low level laser probe properly.

According to an aspect of the present invention, there is provided a method for controlling a low level laser probe suitable for treating adult stem cells of a subject. The low level laser probe has a plurality of light sources provided in a doming treatment surface. The method comprises the steps of:

a. providing status information from a subject;

b. in accordance with the status information provided, controlling the laser probe to transmit light having at least two various wavelengths for stimulating adult stem cells of the subject. At least one first light source is centrally positioned in the doming treatment surface of the probe and is adapted to transmit light of a first wavelength of a first particular intensity and the other light sources positioned around the first light source are adapted to transmit light of another higher wavelength and at least a second higher intensity.

According to another aspect of the present invention, there is provided a control apparatus for controlling a low level laser probe suitable for treating adult stem cells of a subject. The probe has a plurality of light sources provided in a doming treatment surface. The control apparatus is configured to receive and store status information from a subject and configured to control the laser probe to transmit light having at least two various frequencies for stimulating adult stem cells of the subject in accordance with the status information received. At least one first light source is centrally positioned in the doming treatment surface of the probe and is adapted to transmit light of a first wavelength of a first particular intensity and the other light sources positioned around the first light source are adapted to transmit light of another higher wavelength and at least a second higher intensity.

Herein, the term "higher wavelength" includes "longer wavelength".

By means of the present invention, wherein the low level laser probe is controlled and adapted to transmit light of at least two wavelengths improved control of energy transmitted is obtained compared to prior art methods and apparatus. This improved control assists treating stem cells. The light sources being adapted and controlled to transmit light of a higher wavelength and higher intensity, i.e. more energy, than the first centrally positioned light source are considered to influence the stem cells to "open up", or in other words be stimulated to better receive light from the first light source such that the stem cells of the subject can be treated more easily. This is a surprising and new effect that has according to our best knowledge not been disclosed before.

According to an embodiment of the present invention, the control apparatus further comprises a processor, a data base, and a program memory. The program memory comprises computer program instructions when run in the processor configured to store status information from the subject in the data base.

Status information from one or more subject(s) can be provided by means of providing the data base with collected patient data and storing the patient data before receiving status information therefrom. In this way, status information from a particular subject's history, but also from other subjects can be used to improve control of the laser probe in that the most efficient wavelengths, intensity and duration of light can be used based on learned knowledge.

Preferred embodiments are set forth in the dependent claims.

SHORT DESCRIPTION OF THE APPENDED DRAWINGS

Figure 2A:
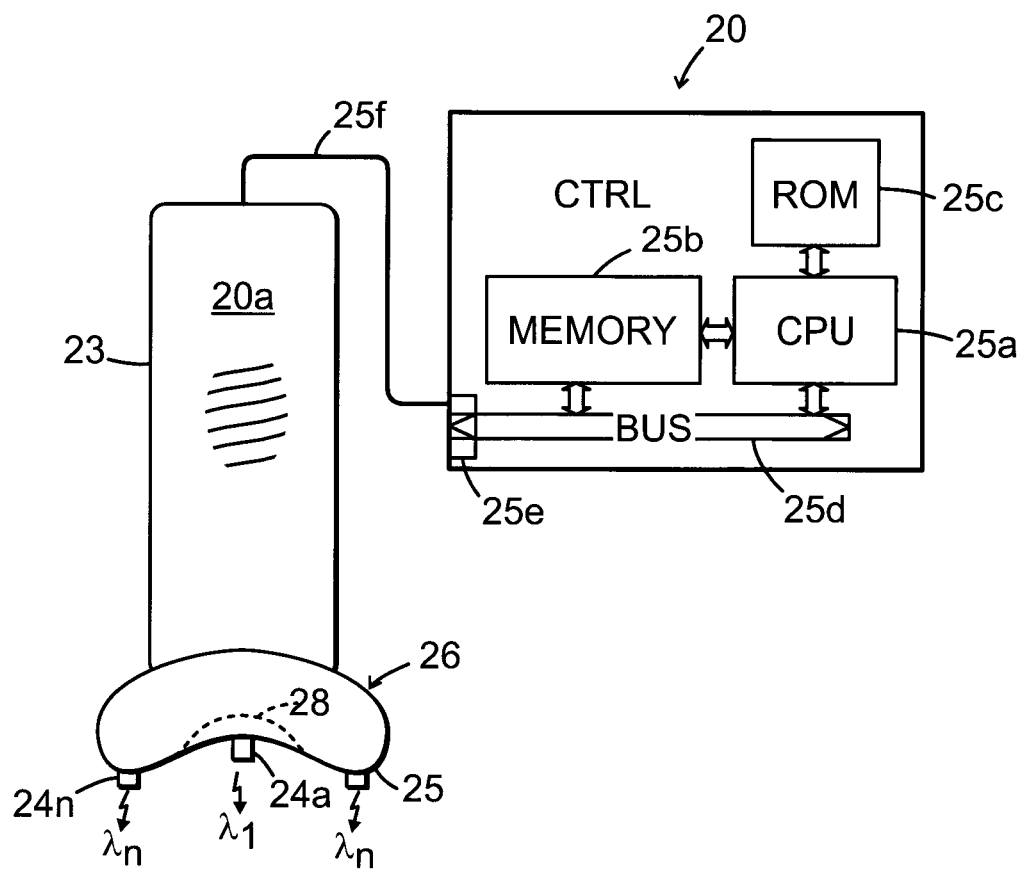
Figure 2B:
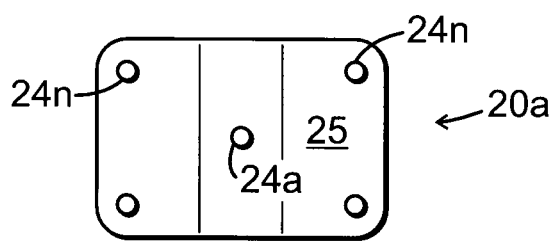

FIG. 1 illustrates a flow-chart of a method according to an embodiment of the present invention, FIG. 2a is a schematic view of an apparatus for controlling a low level laser probe according to an embodiment of the present invention; and FIG. 2b is a bottom view of the low level laser probe per se.

DETAILED DESCRIPTION OF PREFERRED EMBODIMENTS OF THE INVENTION

The invention according to an embodiment of the present invention provides an apparatus for controlling a low level laser probe, that when in use is used to treat, in particular bio-stimulate, bodily ailments (animals are not excluded). The low level laser probe can be used both for the treatment of diseases and for preventative purposes, also in combination with conventional techniques for treatment such as chemotherapy. Conventional techniques such as using x-ray, or blood sampling for confirming treatment can be used.

The invention can also be used for preventive purposes since it is non-destructive or dangerous for the subject treated. In this way, the invention can be used in a very early stage to treat illness such as spread cancers.

The invention is not limited to the use of only one low level laser probe, but alternatively, according to another embodiment of the present invention, two low laser probes can be employed. This embodiment shortens the time required for treatment.

Typically, the two low level laser probes are identical and are controlled to co-operate with each other.

In the following, the invention, in the form of an apparatus for controlling the laser probe and its embodiments will be described as an apparatus comprising a laser probe designed for treatment of a spine as a body structure, but the present invention is not for that reason limited only to be suitable for the spine, and other uneven body structures or deformations can be considered for treatment by the probe.

Now is referred to FIG. 1 and FIG. 2a-b, wherein FIG. 1 illustrates a flow-chart of a method according to an embodiment of the present invention and FIG. 2a is a schematic view of a control apparatus 20 for controlling a low level laser probe 20a according to an embodiment of the present invention; and FIG. 2b is a bottom view of the laser probe used by the present invention.

To start, if not already performed, a subject's, herein a patient's, status information, typically the patient's medical history, is received and stored 11a by means of the control apparatus 20 for controlling a low level laser probe and/or partially by means of any other separate means such as a patient data register, whereby it is important to determine and register how a disease has commenced. This is related to the fact that the first healing effects of a treatment with a low level laser probe typically arise in that area of the body that was last attacked by the disease.

Then, in accordance with the status information provided 11, a low level laser probe 20a is controlled 12, and adapted to transmit light having at least two various wavelengths $\lambda_1$ and $\lambda_n$ for stimulating adult stem cells of the subject (not shown). At least one first light source 24a is centrally positioned in a doming (curved) treatment surface 25 of a laser probe 20a. The laser probe 20a is by means of a first light source 24a adapted to transmit light, visible or not, of a first wavelength $\lambda_1$ of a first particular intensity and the other light sources 24n positioned around the first light source 24a are adapted to transmit light of another second higher wavelength $\lambda_n$ and at least a second higher intensity $I_2$. Different, higher intensities may be applied. The number of second laser light sources 24n can be four (4) for instance, but also any other, typically a higher number of second laser light sources 24n such as five or more.

According to an embodiment of the invention, the laser probe 20a has a handgrip 23 and a foot 26. The foot 26 comprises first and second laser light sources 24a, 24n such as light-emitting diodes as described in the published patent application WO-A1-0121256 by the same applicant. The doming treatment surface 25 is of such a shape that it is adapted in the best possible way to the area of the subject's body on which it is intended to be used for laser treatment. The doming treatment surface 24 is typically flexible, that is:

it can be made from some known material that is elastic or resilient, but which can even then hold laser devices and light devices. The resilient or flexible property of the material used has been indicated with a dotted line 28 in FIG. 2a.

According to an embodiment of the present invention, the control apparatus 20 further comprises a processor 25a, a data base 25b for storing and providing status information of a subject, and a program memory 25c comprising computer program instructions when run in the processor 25a configured to store or provide status information of the subject in the data base 25b. Typically, communication between the probe 20a and the control apparatus is performed by means of a data bus 25d, input/output means 25e and an information carrier 25f such as a cable.

FIG. 2b shows the foot 26 of the low level laser probe 20a viewed from beneath so that the doming treatment surface 25 appear, whereby the doming treatment surface 25 between the solid cross-lines is made clear. The doming treatment surface 25 can in one embodiment be rectangular, for example 4.0*3.5 cm, and slightly concave, that is: it can be adapted to, for example, the spine, and comprise five laser light sources 24a, 24n. Two of the laser light sources 24n are arranged along each short/long side of the doming treatment surface 25, and one of the laser light sources, the first light source, 24a is arranged in the center of the doming surface 25. With this arrangement of the light sources 24a, 24n all treatment areas are reached simultaneously, wherein the second light sources 24n have higher intensity than the first light source 24a, whereby what is known as the output power of the treatment becomes better and the reaction of a patient to the treatment can be determined even while the treatment is being performed. This makes it possible for the first time in the field of low level laser treatment to accommodate, design and modify the treatment in real-time with respect to both content and time, following the pattern of reaction of an individual patient, during the actual treatment session such that communication on a cell-level can be obtained. According to our best understanding, the communication on the cell-level stimulates the subject's own immune defense.

In the following a number of examples will be explained in more detail.

A first stage of a typical laser treatment, in this case of MS, is to treat the spine. The region between vertebrae is treated with 2,500 mW for 5 minutes. Thereafter the region from C1 to the sacrum is treated with 5,000 mW for 5 minutes, and a further 5 minutes from C1 to the sacrum with 2,500 mW. The patient thereafter lies on his or her back for treatment of the frontal lobe from temple to temple with 5,000 mW for 4 minutes.

If a patient has reduced mobility in the legs, the feet should also be treated to stimulate blood circulation, whereby 5,000 mW is applied for 5 minutes to each foot. It is important to be careful that treatment of the feet does not continue for too long so that too much of the energy is transferred to the feet, whereby the principal healing is not achieved in the spine or frontal lobe.

After the laser treatment, a patient can feel heat as a sensation accompanied by tingling, which is often described as light pin-pricks or prickling in the arms and legs. These treatment effects can move around in the body, whereby most reactions arise in the area of the spine. This is a proof of the laser treatment healing the patient.

Each laser treatment takes approximately 30-45 minutes. Typically, the first ten treatments should be carried out at a frequency of two times per week. Noticeable results of the treatments normally arise after approximately 8-10 treatments.

The invention may also be used for treating diseases of the skin or other barrier tissues with a non-destructive low level laser, where the other barrier tissue includes the lining of the mouth, nose, trachea, bronchi, lung, esophagus, stomach, gut, peritoneum, bladder, urethra, penis, prostate, uterus, vagina, arteries, veins or capillaries.

It has been shown that patients follow the same pattern of experiences, independent of age, gender or degree of advancement of their disease. After completion of treatment, a patient can feel active with a pleasant feeling of warmth in the body, or tiredness with a feeling of muscular pains.

One permanent or long-term effect of the treatment against MS is that patients have achieved a noticeable improvement in movement and breathing organs together with an increase in general energy.

In the apparatus of the invention, the light sources operate with light in a pulsed manner (laser light). The pulse duration of the laser light is about 0.1 to about 200 nanoseconds (ns), about 0.5 to 50 ns, or about 1 to 10 ns. The frequency of the laser light is about 1 Hertz (Hz) to about 100 kilo Hertz (kHz), about 0.1 to about 20 kHz, about 1 to about 10 kHz; the irradiance of the laser light is about 0.1 to 10 kHz.

The power of the laser sources is typically within the interval of 1 to 4 W/cm$^2$. Treatment durations of the laser are up to 45 minutes. Treatment may involve a single treatment or a series of treatments up to about 10. Lasers for use in the methods of the invention include emits light in the range of visible light.

Appropriate laser light sources for the method of the invention can include but are not limited to krypton (416 nanometers (nm)), argon (488 and 515 nm), copper bromide (510 and 578 nm), helium-neon (544, 594 and 612 nm), neodymium-doped yttrium aluminum garnet (532 and 1064 nm), ruby (628 and 694 nm), titanium-sapphire (700-1000 nm), neodymium-doped yttrium lithium fluoride (1047 and 1053 nm), erbium-glass (1540 nm), and helium-doped fluoride (2950 nm). Laser wavelengths for use in the methods of the invention include, but are not limited to 510 nm and 578 nm, 532 nm, 810 nm, 1064 nm, 1460, 1540, and 2950 nm. Laser beam sizes for use in the method of the invention include, but are not limited to 1-10 mm, 2-8 mm, 2-7 mm, or 3-5 mm in diameter.

As used herein "treating" a disease in a subject or "treating" a subject having a disease refers to subjecting the subject to a laser exposure, in such a manner that the extent of the disease is decreased or prevented. For example, treating results in the reduction of at least on sign or symptom of the disease or condition. Treatment includes (but is not limited to) administration of an exposure to a laser as described herein subsequent to the initiation of a pathologic event. Treatment can require administration of an agent and/or treatment more than once.

As used herein, a "condition" includes any abnormality that can occur in a subject including any disease, infection, disorder, tumor, cancer, inflammation, or change in cellular structure and function.

As used herein, "subject" refers to a mammal. A human subject can also be known as a patient. As used herein, "mammal" refers to any mammal including but not limited to human, mouse, rat, sheep, monkey, goat, rabbit, hamster, horse, cow or pig. A "non-human mammal," as used herein, refers to any mammal that is not a human. As used herein "exposure" means treating with a laser for a time useful to the invention. In one embodiment, exposure means to treat with a laser applied in a pulse, wherein the pulse is applied for a particular duration. The range of pulse durations are in the hundreds of picoseconds to hundreds of nanoseconds (for example, about 100, 200, 300, 400, 500, 600, 700, 800, 900 picoseconds, or about 1, 2, 3, 4, 5, 6, 7, 8, 9, 10, 12, 15, 20, 25, 30, 35, 40, 45, 50, 75, 100, or 200 nanoseconds). It is understood that the actual pulse length will vary somewhat based on the limitations of the laser and the switching rate/shutter speed. In another embodiment, "exposure" means to treat with a laser of a particular pulse repetition (pulse frequency). Optimal pulse frequencies range from about 1 Hz to about 100 kHz (for example, 0.001, 0.01, 1, 10, 100 kHz), with typical pulse frequencies in the 1, 2, 3, 4, 5, 6, 7, 8, 9, 10, 20, 30, 40, 50 or 100 kHz frequency. It is understood that the actual pulse frequency will vary somewhat based on the limitations of the laser and the switching rate/shutter speed. In another embodiment, "exposure" means to treat with a laser of a particular wavelength where the range of wavelengths can range from the visible light to the mid-infrared portion of the electromagnetic spectrum (approximately 500 nm to 3000 nm, for example, 400, 425, 450, 475, 500, 525, 550, 575, 600, 625, 650, 675, 700, 725, 750, 775, 800, 825, 850, 875, 900, 925, 950, 975, 1000, 1125, 1150, 1175, 1200, 1225, 1250, 1275, 1300, 1325, 1350, 1375, 1400, 1500, 1600, 1700, 1800, 1900, 2000, 2100, 2200, 2300, 2400, 2500, 2600 2700 2800, 2900, and 3000 nm), and are typically about 500-2000 nm. In another embodiment, "exposing" means to expose a subject to a laser with a particular peak energy, where the range of pulse energy is 1 micro joule to ($1\times10<"6>$J) to 1 Joule (for example, 1, 10, 20, 30 40, 50, 100, 200, 300, 400, 500 micro joules. 1, 2, 3, 4, 5, 10, 20, 30, 40, 50, 100, 200, 300, 400 500 milli joules, or 0.6, 0.7, 0.8, 0.9, and 1.0 Joule).

In another embodiment, "exposure" means to treat with a laser of a particular power density or irradiance, where the range of irradiance is 0.1 to 10 W/cm$^2$ (for example, about 0.1, 0.2, 0.3, 0.4, 0.5, 0.6, 0.7, 0.8, 0.9, 1, 2, 3, 4, 5, 6, 7, 8, 9, or 10 W/cm) and are typically about 1-4 W/cm$^2$.

In another embodiment, "expose" means to treat with a laser for a particular length of time. The range of exposure times can be about 10 seconds to about 600 seconds (for example, about 10, 20, 30, 40, 50, 60, 70, 80, 90, 100, 150, 200, 250, 300, 350, 400, 450, 500, 550, 600 seconds).

In another embodiment, "exposure" means to treat with a laser a particular area of the subject. Typical treatment areas are about 1-100 mm in diameter (for example, 1, 2, 3, 4, 5, 6, 7, 8, 9, 10, 20, 30, 40, 50, 60, 70, 80, 90 and 100 mm$^2$). Treatment may involve exposure of multiple areas of the subject. As used herein, a "laser" refers to an electronic-optical device that emits coherent light radiation. A typical laser emits light in a narrow, low-divergence monochromatic (single-colored, if the laser is operating in the visible spectrum), beam with a well-defined wavelength.

As used herein, a "laser" includes any laser that is currently available or may become available that can provide the appropriate pulse duration, power, and pulse frequency required by the methods of the instant invention. Currently available lasers that can be used in the methods of the invention include, but are not limited to gas vapor lasers, metal vapor lasers, pulse dye lasers, solid state lasers, semiconductor lasers and fiber lasers. Examples of lasers that can provide appropriate pulse duration, power density, and pulse frequency include a copper bromide laser such as the Norseld Dual Yellow copper bromide laser (511 and 578 nm) or the Asclepion ProYellow+ copper (511 and 578 nm), a Q-switched neodymium-doped yttrium aluminum garnet (Nd: YAG) laser such as the RMI 15 Q-Switched Diode-Pumped Solid State Laser with an output at either 532 nm or 1064 nm, a Q-switched Alexandrite laser at 755 nm, a Q-switched 810 nm diode laser, a pulsed fiber laser such as the IPG Photonics YLP series ytterbium pulsed fiber laser at 1055-1075 nm, or a nanosecond pulsed fiber laser such as the Nufern NuTx erbium-ytterbium doped 1550 nm nanosecond pulsed fiber laser.

The invention has as its goal the strengthening of the body's inherent defence mechanisms. The major successes of the inventive treatment are the cases where the patients have overcome their illness through the mobilisation of their own resources, that is, through a strengthened immune response of such a magnitude that the illness has been overcome and disappeared. The inventive method and apparatus can, in addition to conventional techniques, also be used to augment the effects of other forms of treatment such as radiotherapy and cytostatic therapy in the treatment of cancer.

One possible explanation for the efficacy of the treatment could be that it affects the production or concentration of antibodies through inter-cellular communication. It can be seen as a means of re-establishing a normal cellular communication that has been compromised by illness or injury.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A low level laser probe apparatus for treating adult stem cells of a subject, the low level laser probe apparatus comprising:
    a low level laser probe having a doming treatment surface and a plurality of light sources provided in the doming treatment surface, and
    a controller for controlling the low level laser probe for real-time treatment of the adult stem cells of the subject;
    wherein the controller is configured to store and receive status information from a subject and wherein the controller is configured to control the laser probe to transmit light having at least two different wavelengths for stimulating adult stem cells of the subject in accordance with the status information received,
    wherein the plurality of light sources include at least one first light source that is centrally positioned in the doming treatment surface of the probe and is adapted and controlled by the controller to transmit light of a first wavelength of a first intensity and the plurality of light sources include other light sources positioned around the first light source and adapted and controlled by the controller to transmit light of a second wavelength higher than the first wavelength and at least a second intensity higher than the first intensity; and
    wherein the controller is configured to modify the treatment in real-time with respect to both content and time, during an actual treatment session.

2. The low level laser probe apparatus according to claim 1, wherein the controller includes a processor, a data base, and a program memory comprising computer program instructions when run in the processor configured to store status information from the subject in the data base.

3. The low level laser probe apparatus according to claim 2, wherein the doming treatment surface has a rectangular shape with four of said other light sources positioned proximate respective corners of the doming treatment surface.

4. The low level laser probe apparatus according to claim 1, wherein the doming treatment surface has a rectangular shape with four of said other light sources positioned proximate respective corners of the doming treatment surface.

5. The low level laser probe apparatus according to claim 1, wherein the doming treatment surface has sides intersecting at corners, and the other light sources are respectively positioned proximate said corners.

* * * * *